United States Patent
Lou et al.

(10) Patent No.: US 10,092,267 B2
(45) Date of Patent: Oct. 9, 2018

(54) GENERATING MATERIAL HARDENING EFFECT DATA

(71) Applicant: Shenyang Neusoft Medical Systems Co., Ltd., Shenyang (CN)

(72) Inventors: Shanshan Lou, Shenyang (CN); Gang Fang, Shenyang (CN); Jiangwei Zhao, Shenyang (CN)

(73) Assignee: SHENYANG NEUSOFT MEDICAL SYSTEMS CO., LTD., Shenyang (CN)

( * ) Notice: Subject to any disclaimer, the term of this patent is extended or adjusted under 35 U.S.C. 154(b) by 388 days.

(21) Appl. No.: 14/972,104

(22) Filed: Dec. 17, 2015

(65) Prior Publication Data

US 2016/0183904 A1 Jun. 30, 2016

(30) Foreign Application Priority Data

Dec. 30, 2014 (CN) .......................... 2014 1 0843296

(51) Int. Cl.
*A61B 6/00* (2006.01)

(52) U.S. Cl.
CPC ............ *A61B 6/583* (2013.01); *A61B 6/5205* (2013.01)

(58) Field of Classification Search
CPC ......... A61B 6/5205; A61B 6/583; A61B 6/03; A61B 6/032; A61B 6/4035; A61B 6/5258; A61B 6/542; A61B 6/544; A61B 6/482; A61B 6/502; A61B 6/481; A61B 6/505; A61B 6/06; A61B 6/4014; A61B 6/4085; A61B 6/488; A61B 6/507; A61B 6/5235;

(Continued)

(56) References Cited

U.S. PATENT DOCUMENTS

2005/0013414 A1 1/2005 Sun et al.
2007/0086561 A1 4/2007 Bruder et al.
(Continued)

FOREIGN PATENT DOCUMENTS

CN 1483383 A 3/2004
CN 1765324 A 5/2006
(Continued)

OTHER PUBLICATIONS

Beam hardening correction using a conical water-equivalent phantom for preclinical micro-CT; Deng, J.; Shikui Yan; Mu Chen; Bruckbauer, T.; Nuclear Science Symposium and Medical Imaging Conference (NSS/MIC), 2011 IEEE, p. 2922-2924.
(Continued)

*Primary Examiner* — Irakli Kiknadze
(74) *Attorney, Agent, or Firm* — Kilpatrick Townsend & Stockton, LLP (57) ABSTRACT

A method for generating material hardening effect data is provided. Actual X-ray attenuation values of a universal phantom corresponding to different angles at each of channels may be obtained. Equivalent filtration thicknesses corresponding to each of the channels may be determined according to theoretical X-ray attenuation values and the actual X-ray attenuation values corresponding to different angles at each of the channels. Hardening effect data corresponding to a material may be generated according to a predetermined length of the material, a number of sampling points and the equivalent filtration thicknesses corresponding to each of the channels.

12 Claims, 4 Drawing Sheets

(58) Field of Classification Search
CPC ..... A61B 6/5264; A61B 6/527; A61B 6/5282;
A61B 6/54; A61B 6/4241; A61B 6/4266;
A61B 6/027; A61B 6/035; A61B 6/12;
A61B 6/42; A61B 6/4208; A61B 6/4233;
A61B 6/4275; A61B 6/4435; A61B 6/04;
G06T 11/005; G06T 2211/408; G06T
2211/424; H05G 1/26
USPC ...................................... 378/4, 5, 18, 19, 60
See application file for complete search history.

(56) References Cited

U.S. PATENT DOCUMENTS

| | | | |
|---|---|---|---|
| 2007/0092056 A1* | 4/2007 | Flohr .................... | A61B 6/032 378/4 |
| 2007/0189444 A1* | 8/2007 | Van Steven-Daal ........................ | A61B 6/032 378/6 |
| 2008/0095302 A1 | 4/2008 | Ruhrnschopf et al. | |
| 2010/0183214 A1* | 7/2010 | McCollough .......... | A61B 6/032 382/131 |
| 2010/0195804 A1 | 8/2010 | Dafni et al. | |
| 2011/0168878 A1 | 7/2011 | Hoerndler et al. | |
| 2015/0348258 A1* | 12/2015 | Petschke .............. | G06T 7/0012 382/131 |
| 2016/0157809 A1* | 6/2016 | Takahashi ............ | A61B 6/5258 378/16 |
| 2016/0242726 A1* | 8/2016 | Koehler ................ | A61B 6/032 |

FOREIGN PATENT DOCUMENTS

| | | |
|---|---|---|
| CN | 1879560 A | 12/2006 |
| CN | 101226642 A | 7/2008 |
| EP | 1389444 A1 | 2/2004 |
| EP | 1635296 A1 | 3/2006 |
| EP | 2133840 A2 | 12/2009 |
| JP | 2006-334319 A | 12/2006 |

OTHER PUBLICATIONS

A generalized model for the conversion from CT numbers to linear attenuation coefficients; Chuanyong Bai; Ling Shao; Da Silva, A.J.; Zuo Zhao; IEEE Transactions on nuclear science, vol. 50, Issue: 5, Oct. 2003, p. 1510-1515.

Beam hardening correction for fan-beam CT imaging with multiple materials; Yanbo Zhang; Xuanqin Mou; Shaojie Tang; Nuclear Science Symposium Conference Record (NSS/MIC), 2010 p. 3566-3570.

Fu jiang, Lu hongnian, et al. Harden correction based on original projection sinogram for X-CT. Journal of Beijing University of Aeronautics and Astronautics, 2006, vol. 32 No. 6: 725-728.

Zhang J, Li L, Zhang F, et al. Review of the methods for beam hardening correction in X-ray computed tomography[J]. CT Theory and Applications, 2013, 22(1): 195-204.

* cited by examiner

FIG. 1

( Abstract Figure )

GENERATING MATERIAL HARDENING EFFECT DATA

The present application claims the priority to Chinese Patent Applications No. 201410843296.3, filed with the Chinese State Intellectual Property Office on Dec. 30, 2014, which is incorporated herein by reference in its entirety.

BACKGROUND

The present disclosure is directed to medical technology.

Under medical scenes, such as spectroscopy imaging decomposition and material hardening artefact removal, etc., material hardening effect data usually should be known. Typically, the material hardening effect data can be obtained by performing CT scan on a specially-designed phantom.

Generally speaking, the specially-designed phantom requires higher manufacturing process, and consumes more manufacturing time and cost. Additionally, after the specially-designed phantom is manufactured, its material composition and size have been fixed and only hardening effect data corresponding to the particular material and the particular size can be obtained. Therefore, the abovementioned method has certain limitations, which cannot meet actual demands.

NEUSOFT MEDICAL SYSTEMS CO., LTD. (NMS), founded in 1998 with its world headquarters in China, is a leading supplier of medical equipment, medical IT solutions, and healthcare services. NMS supplies medical equipment with a wide portfolio, including CT, MRI, digital X-ray machine, Ultrasound, PET (Positron Emission Tomography), Linear Accelerator, and Biochemistry Analyser. Currently, NMS' products are exported to over 60 countries and regions around the globe, serving more than 5,000 renowned customers. NMS's latest successful developments, such as 128 Multi-Slice CT Scanner System, Superconducting MRI, Linear Accelerator, and PET products, have led China to become a global high-end medical equipment producer. As an integrated supplier with extensive experience in large medical equipment, NMS has been committed to the study of avoiding secondary potential harm caused by excessive X-ray irradiation to the subject during the CT scanning process.

BRIEF DESCRIPTION OF DRAWINGS

Features of the present disclosure are illustrated by way of example and not limited in the following figure(s), in which like numerals indicate like elements, in which.

DETAILED DESCRIPTION

For simplicity and illustrative purposes, the present disclosure is described by referring mainly to an example thereof. In the following description, numerous specific details are set forth in order to provide a thorough understanding of the present disclosure. It will be readily apparent however, that the present disclosure may be practiced without limitation to these specific details. In other instances, some methods and structures have not been described in detail so as not to unnecessarily obscure the present disclosure. As used herein, the terms "a" and "an" are intended to denote at least one of a particular element, the term "includes" means includes but not limited to, the term "including" means including but not limited to, and the term "based on" means based at least in part on.

Figure 1:
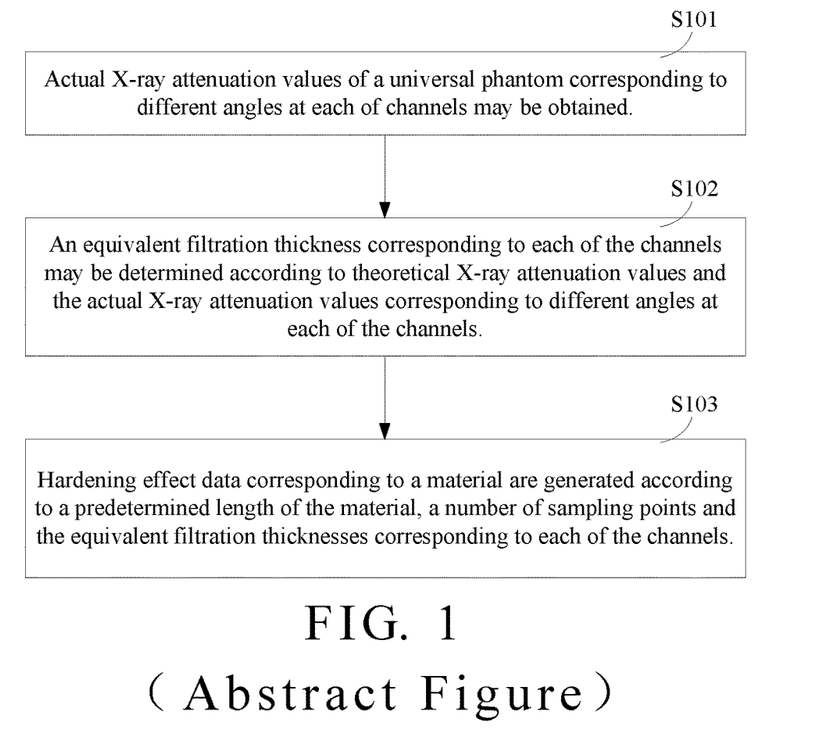
FIG. 1 is a flowchart illustrating a method for generating material hardening effect data according to an example of the present disclosure.

FIG. 1 is a flowchart illustrating a method for generating material hardening effect data according to an example of the present disclosure. The method may include the following blocks S101~S103.

At block S101, actual X-ray attenuation values of a universal phantom corresponding to different angles at each of channels may be obtained.

In an example, scan data may be obtained by scanning the universal phantom. Generally speaking, the scan data obtained by scanning the universal phantom are the actual X-ray attenuation values $P_k(v)$ of the universal phantom corresponding to different angles at each of channels, wherein k represents a scanning channel index, and k=1~K ((i.e., total K channels); v represents an angular position index of the bulb, and v=1~V (i.e., total V angular positions in a scanning circle).

Since the actual X-ray attenuation values of the universal phantom are usually used in many application scenarios, a user may pre-store the actual X-ray attenuation values of the universal phantom in advance. In this case, the actual X-ray attenuation values of the universal phantom pre-stored by the user can be directly obtained. The so-called universal phantom refers to a commonly-used phantom containing a single material, such as a cylindrical water phantom, a cylindrical plexiglass phantom, and the like.

At block S102, an equivalent filtration thickness corresponding to each of the channels may be determined according to theoretical X-ray attenuation values and the actual X-ray attenuation values corresponding to different angles at each of the channels.

In the following, a brief introduction for absorption of X-ray beam in the actual scanning process is described first.

An X-ray beam emitted by a bulb may usually have a very wide spectrum during scanning process, wherein low-frequency band portion of the X-ray beam may be almost absorbed by the subject (such as human body), and it basically does not contribute to the detection signal. Additionally, the section of the subject may be generally elliptical-shaped, and thus it may be necessary to adjust X-ray intensities of different channels. In order to eliminate low-frequency band X-ray beam and reduce surface radiation dose of the subject, a filter is usually mounted on CT machine for improving the quality of X-ray beam. The filter thicknesses corresponding to different channels are unequal, so that the spectrum of X-ray beam may be different after X-ray beam passes through different filters of different channels, which causes different hardening effects at different channels. In order to calculate hardening effect data corresponding to the material, the lengths of the filters passed by X-ray beam corresponding to each of the channels may be determined first, that is to say, equivalent filtration thicknesses corresponding to each of the channels shall be determined firstly.

In specific implementation, the equivalent filtration thicknesses corresponding to each of the channels may be determined in such a way that may minimize errors between the theoretical X-ray attenuation values and the actual X-ray attenuation values corresponding to different angles at each of the channels. For example, Least Squares algorithm may be used to obtain the equivalent filtration thicknesses corresponding to each of the channels, or iterative algorithm may be adopted for obtaining the equivalent filtration thicknesses corresponding to each of the channels.

Be noted that, as long as the errors between the theoretical X-ray attenuation values and the actual X-ray attenuation values corresponding to different angles at each of the channels may be minimized, any algorithm may be used to obtain the equivalent filtration thicknesses corresponding to each of the channels and this should not be a limitation in the example of the present disclosure.

At block S103, hardening effect data corresponding to a material are generated according to a predetermined length of the material, a number of sampling points and the equivalent filtration thicknesses corresponding to each of the channels.

In an example, hardening effect data corresponding to a material may be generated based on the following equation:

$$P_k(L_1) = \ln\left(\sum_{i=1}^{N} I_0(i) * \exp(-\mu_{filter}(i) * L_{filter,k} - \mu_{filter}(i) * (D - L_{filter,k}))\right) - \ln\left(\sum_{i=1}^{N} I_0(i) * \exp(-\mu_{filter}(i) * L_{filter,k} - \mu_{air}(i) * L_{air} - \mu_1(i) * L_1)\right).$$

Herein $P_k(L_1)$ represents the hardening effect data corresponding to the material at the $k^{th}$ channel, and k represents a channel index;

$I_0(i)$ represents the $i^{th}$ spectral intensity value of X-ray beam emitted by the bulb, i=1~N, and N represents an aliquot number of X photons with various energy levels contained in the X-ray beam;

$\mu_{filter}(i)$ represents an attenuation coefficient of the $i^{th}$ spectrum corresponding to a filter;

$L_{filter,k}$ represents the equivalent filtration thickness corresponding to the $k^{th}$ channel;

$\mu_{air}(i)$ represents an attenuation coefficient of the $i^{th}$ spectrum corresponding to air;

$\mu_1(i)$ represents an attenuation coefficient of the $i^{th}$ spectrum corresponding to the material;

$L_1$ represents a predetermined length of the material;

$L_{air}$ represents a predetermined length of air; and

D represents a distance between the bulb and a detector.

In another example, hardening effect data corresponding to two or more materials may be generated based on the following equation:

$$P_k(L_1, \ldots, L_M) = \ln\left(\sum_{i=1}^{N} I_0(i) * \exp(-\mu_{filter}(i) * L_{filter,k} - \mu_{filter}(i) * (D - L_{filter,k}))\right) - \ln\left(\sum_{i=1}^{N} I_0(i) * \exp(-\mu_{filter}(i) * L_{filter,k} - \mu_{air}(i) * L_{air} - \mu_1(i) * L_1 \ldots - \mu_M(i) * L_M).$$

Herein $P_k(L_1, \ldots, L_M)$ represents the hardening effect data corresponding to M materials at the $k^{th}$ channel, k represents a channel index, M represents a number of species of materials, and M is an integer greater than 1;

$I_0(i)$ represents the $i^{th}$ spectral intensity value of X-ray beam emitted by the bulb, i=1~N, and N represents an aliquot number of X photons with various energy levels contained in the X-ray beam;

$\mu_{filter}(i)$ represents an attenuation coefficient of the $i^{th}$ spectrum corresponding to a filter;

$L_{filter,k}$ represents the equivalent filtration thickness corresponding to the $k^{th}$ channel;

$\mu_{air}(i)$ represents an attenuation coefficient of the $i^{th}$ spectrum corresponding to air;

$\mu_1(i)$ represents an attenuation coefficient of the $i^{th}$ spectrum corresponding to the first material;

$\mu_M(i)$ represents an attenuation coefficient of the $i^{th}$ spectrum corresponding to the $M^{th}$ material;

$L_1$ represents a predetermined length of the first material, and $L_M$ represents a predetermined length of the $M^{th}$ material;

$L_{air}$ represents a predetermined length of air; and

D represents a distance between the bulb and a detector.

In order to generate the hardening data corresponding to two or more materials, the length of each material and the number of sampling points may be set in advance. For example, if totally M materials are included, numj represents a total number of sampling points corresponding to the $j^{th}$ material. Therefore, totally K*num1*num2* . . . *numM data can be obtained through the abovementioned calculations, that is to say, the number of calculated data is equal to the product of the total number of the channels and the total numbers of the sampling points corresponding to each material.

The equivalent filtration thicknesses corresponding to different channels may be determined by using the actual X-ray attenuation values of the universal phantom. The hardening effect data corresponding to any one or more materials may be determined based on the equivalent filtration thickness(es), the length(s) of the material(s) and the number(s) of sampling points, without scanning a phantom of a special material anymore. Therefore, cost can be saved by adopting the present disclosure. Significantly, the present disclosure has advantages of saving time and saving cost especially under the condition that hardening effect data corresponding to various different materials need to be determined.

Figure 2:
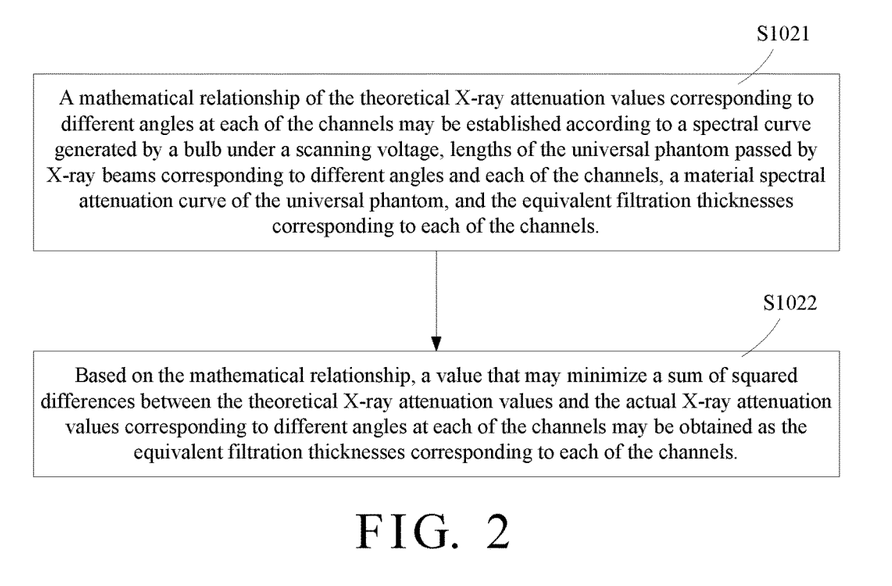
FIG. 2 is a flowchart illustrating a method for calculating equivalent filtration thicknesses corresponding to each of the channels according to an example of the present disclosure.

FIG. 2 is a flowchart illustrating a method for calculating equivalent filtration thicknesses corresponding to each of the channels according to an example of the present disclosure. As shown in FIG. 2, the method may include the following blocks S1021 and S1022.

At block S1021, a mathematical relationship of the theoretical X-ray attenuation values corresponding to different angles at each of the channels may be established according to a spectral curve generated by a bulb under a scanning voltage, lengths of the universal phantom passed by X-ray beams corresponding to different angles and each of the channels, a material spectral attenuation curve of the universal phantom, and the equivalent filtration thicknesses corresponding to each of the channels.

For example, the mathematical relationship may be represented by the following equation:

$$P'_k(v) = \ln\left(\sum_{i=1}^{N} I_0(i) * \exp(-\mu_{filter}(i) * L_{filter,k} - \mu_{air}(i) * (D - L_{filter,k}))\right) -$$

$$\ln\left(\sum_{i=1}^{N} I_0(i) * \exp\right.$$

$$\left.(-\mu_{filter}(i) * L_{filter,k} - \mu_{air}(i) * (D - L_{filter,k} - W_{v,k}) - \mu_{plan}(i) * W_{v,k}\right).$$

Herein $P_k'(v)$ represents the theoretical X-ray attenuation value of the universal phantom corresponding to the $v^{th}$ angle at the $k^{th}$ channel; k represents a channel index, and v represents an angular position index of the bulb;

$I_0(i)$ represents the $i^{th}$ spectral intensity value of X-ray beam emitted by the bulb, i=1~N, and N represents an aliquot number of X photons with various energy levels contained in the X-ray beam;

$\mu_{filter}(i)$ represents an attenuation coefficient of the $i^{th}$ spectrum corresponding to a filter;

$L_{filter,k}$ represents the equivalent filtration thickness corresponding to the $k^{th}$ channel;

$\mu_{air}(i)$ represents an attenuation coefficient of the $i^{th}$ spectrum corresponding to air;

D represents a distance between the bulb and a detector;

$\mu_{plan}(i)$ represents an attenuation coefficient of the $i^{th}$ spectrum corresponding to the material of the universal phantom; and $W_{v,k}$ represents a length of the universal phantom passed by X-ray beam corresponding to the $v^{th}$ angle and the $k^{th}$ channel.

At block S1022, based on the mathematical relationship, a value that may minimize a sum of squared differences between the theoretical X-ray attenuation values and the actual X-ray attenuation values corresponding to different angles at each of the channels may be obtained as the equivalent filtration thicknesses corresponding to each of the channels.

For example, a value meets the following equation can be obtained:

$$\min_{L_{filter,k}} \sum_{v}^{V} [P'_k(v) - P_k(v)]^2.$$

Herein $P_k'(v)$ represents the theoretical X-ray attenuation value of the universal phantom corresponding to the $v^{th}$ angle at the $k^{th}$ channel; and $P_k(v)$ represents the actual X-ray attenuation value of the universal phantom corresponding to the $v^{th}$ angle at the $k^{th}$ channel.

In the abovementioned formula, $P_k'(v)$ only has one unknown parameter $L_{filter,k}$ and thus a value that may minimize a sum of squared differences between the theoretical X-ray attenuation values and the actual X-ray attenuation values corresponding to different angles at each of the channels can be obtained, wherein this value is the equivalent filtration thicknesses corresponding to the $k^{th}$ channel.

$W_{v,k}$ may be obtained by various methods. For example, the center of the universal phantom may be determined according to the geometric relationship, and then the geometric position relationship of the bulb, the rotation center, and the center of the phantom may be used to determine the lengths of the universal phantom passed by X-ray beams corresponding to different angles and each of the channels.

Figure 3:
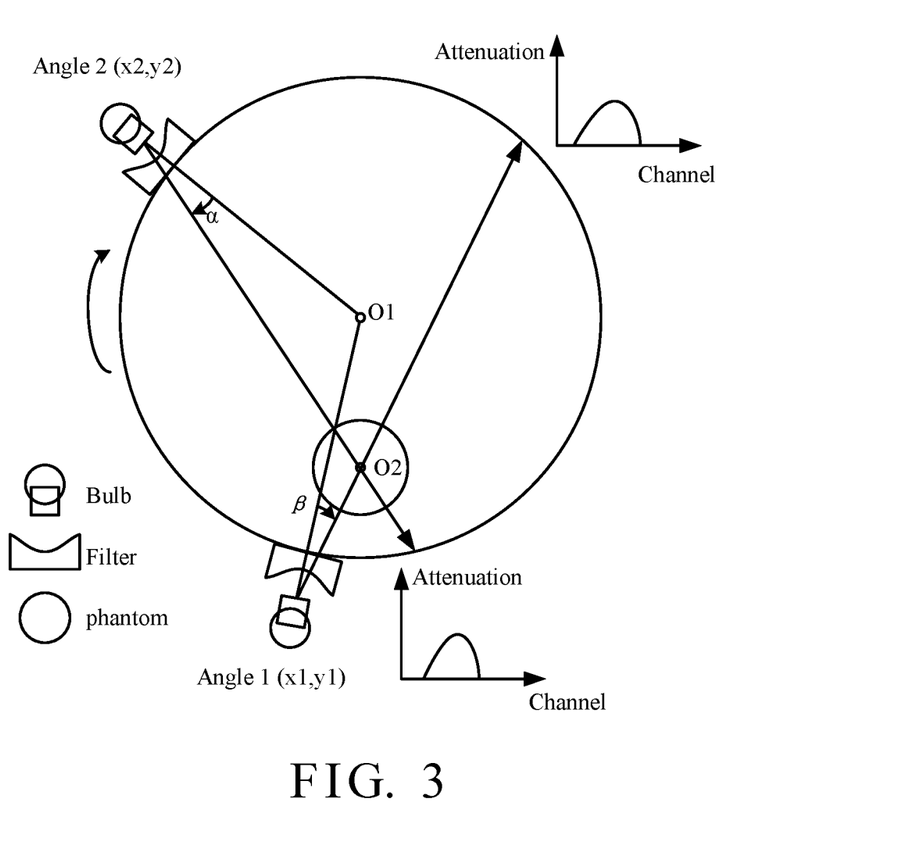
FIG. 3 is a geometric relationship diagram of CT scan according to an example of the present disclosure.

In an example, $W_{v,k}$ may be obtained by using the following method. First, an intersection point of two channels which respectively correspond to maximum actual X-ray attenuation values at two different angles may be determined as a center point of the universal phantom. After that, the lengths of the universal phantom passed by X-ray beams corresponding to different angles and each of the channels may be determined according to the center of the universal phantom, a rotation center and a position of the bulb FIG. 3 is a geometric relationship diagram of CT scan according to an example of the present disclosure. In FIG. 3, Angle 1 and Angle 2 are two arbitrary angles, and the center O2 of the universal phantom may be determined according to two channels which respectively correspond to maximum actual X-ray attenuation values at these two angles. Therefore, the lengths of the universal phantom passed by X-ray beams corresponding to different angles and each of the channels may be determined by using geometric relationship according to the angular position of the bulb, the rotation center O1 and the center O2 of the universal phantom.

In practical application scenarios, to obtain hardening effect data of multiple material is mainly for base material decomposes and hardening correction based on spectroscopy imaging. Take dual-energy material decomposes as an example, after obtaining hardening effect data of multiple material, usually using further algorithm to transform it to the image domain to be processed and performing accurate image segmentation are required in order to achieve solution for the dual-energy material decomposes polynomial.

Figure 4:
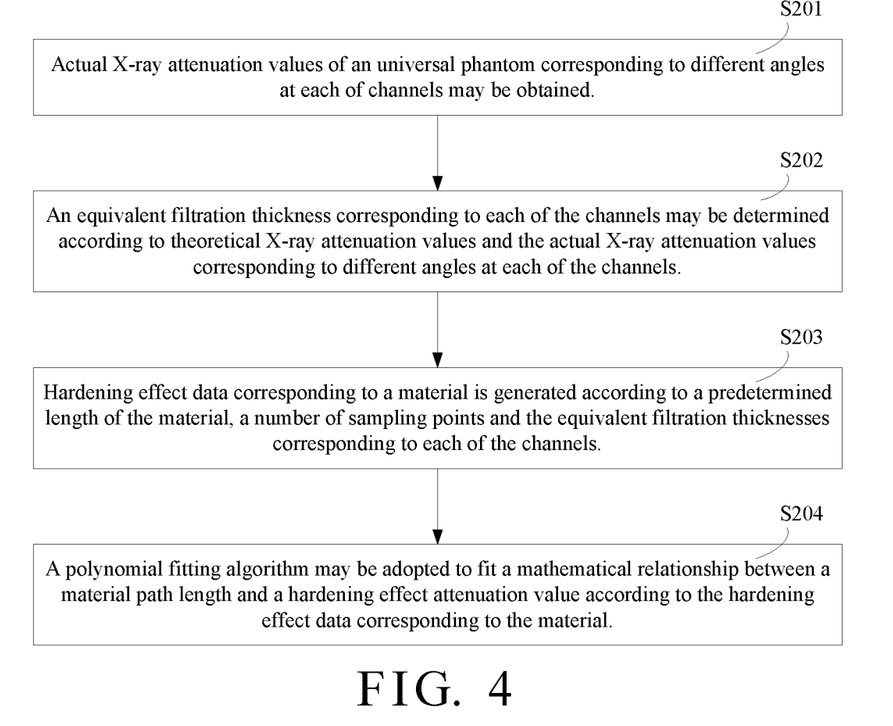
FIG. 4 is a flowchart illustrating a method for generating material hardening effect data according to another example of the present disclosure.

FIG. 4 is a flowchart illustrating a method for generating material hardening effect data according to another example of the present disclosure. FIG. 4 may mainly include the following blocks S201-S204.

At block S201, actual X-ray attenuation values of a universal phantom corresponding to different angles at each of channels may be obtained.

At block S202, an equivalent filtration thickness corresponding to each of the channels may be determined according to theoretical X-ray attenuation values and the actual X-ray attenuation values corresponding to different angles at each of the channels.

At block S203, hardening effect data corresponding to a material is generated according to a predetermined length of the material, a number of sampling points and the equivalent filtration thicknesses corresponding to each of the channels.

The abovementioned blocks S201-S203 are identical to the blocks S101-S103, and thus further descriptions are omitted.

At block S204, a polynomial fitting algorithm may be adopted to fit a mathematical relationship between a material path length and a hardening effect attenuation value according to the hardening effect data corresponding to the material.

The polynomial fitting algorithm may be understood as deriving an analytic function, such that it passes through or approximately passes through a finite sequence's data points to splendidly approach or to fit known data under a certain sense. For example, analytical expressions adapted for the discipline of known data may be used to express the known data, or a continuous curve (surface) may be used to approximately express the function relationship (mathematical relationship) between coordinate values represented by a number of discrete points.

In an example, the hardening effect data corresponding to the material may be used as a number of discrete points in order to fit a curve or a surface, and this curve or this surface may express the relationship between the material path and the hardening effect attenuation values. The hardening effect data corresponding to the sampling points of the material may be obtained through the blocks S201-S203, and the hardening effect data corresponding to the other portion beyond the sampling points of the material may be expressed by the fitted mathematical relationship, which can enrich the hardening effect data corresponding to the material.

Under the case of dual-energy material decomposes, a polynomial fitting may be performed on the hardening effect data of the two energies, respectively. Herein Least Squares algorithm or other solving methods may be used to solve the polynomial coefficients, and the polynomial coefficients may be used as coefficients for decomposing base materials.

According to the above mentioned method for generating material hardening effect data, a device for generating material hardening effect data is provided in the present disclosure. Please refer to FIG. 5. In an example, the device may include a processor such as a CPU 51 and a machine readable storage medium 52, wherein the processor 51 is connected to the machine readable storage medium 52 by an internal bus 53. In other possible implementations, the device may further include an interface 54 for communicating with other devices or components.

Figure 5:
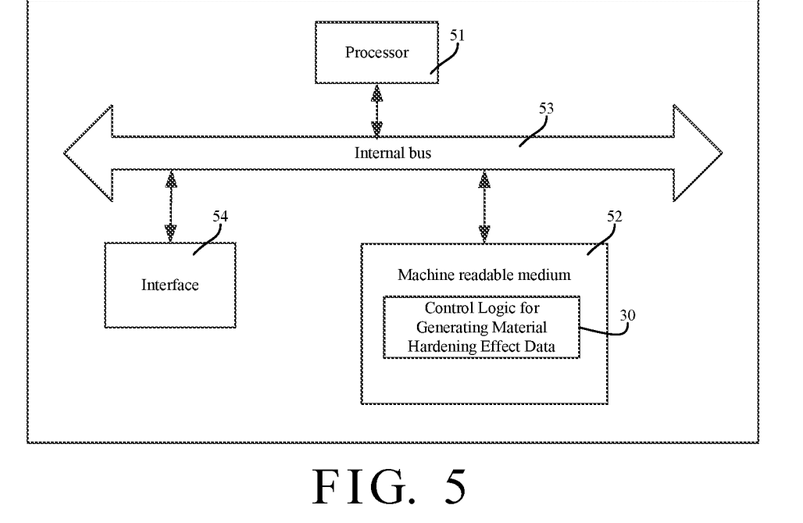
FIG. 5 is a hardware architecture diagram of a device for generating material hardening effect data according to an example of the present disclosure.

In different examples, the machine readable storage medium 52 may be Random Access Memory (RAM), volatile memory, non-volatile memory, flash memory, storage drives (such as, hard drive), solid state drive, any type of storage disks (such as, CD-ROM, DVD, etc.), or similar storage medium, or a combination thereof.

Figure 6:
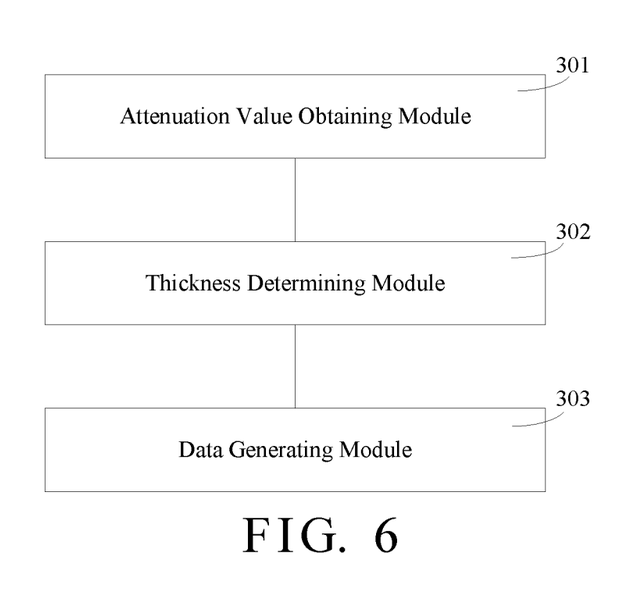
FIG. 6 is a block diagram of the control logic for generating material hardening effect data according to an example of the present disclosure.

Furthermore, the machine readable storage medium 52 is used to store instructions corresponding to a control logic 30 for generating material hardening effect data. As shown in FIG. 6, a block diagram of the control logic 30 may further include an attenuation value obtaining module 301, a thickness determining module 302, and a data generating module 303.

The attenuation value obtaining module 301 is used to obtain actual X-ray attenuation values of a universal phantom corresponding to different angles at each of channels.

The thickness determining module 302 is used to determine equivalent filtration thicknesses corresponding to each of the channels according to theoretical X-ray attenuation values and the actual X-ray attenuation values corresponding to different angles at each of the channels.

The data generating module 303 is used to generate hardening effect data corresponding to a material according to a predetermined length of the material, a number of sampling points and the equivalent filtration thicknesses corresponding to each of the channels.

Specifically, the thickness determining module 302 is used to determine the equivalent filtration thicknesses corresponding to each of the channels in such a way that may minimize errors between the theoretical X-ray attenuation values and the actual X-ray attenuation values corresponding to different angles at each of the channels.

In an example, the thickness determining module 302 may further include an establishing sub-module and a value obtaining sub-module.

The establishing sub-module is used to establish a mathematical relationship of the theoretical X-ray attenuation values corresponding to different angles at each of the channels according to a spectral curve generated by a bulb under a scanning voltage, lengths of the universal phantom passed by X-ray beams corresponding to different angles and each of the channels, a material spectral attenuation curve of the universal phantom, and the equivalent filtration thicknesses corresponding to each of the channels.

The value obtaining sub-module is used to, based on the mathematical relationship, obtain a value that may minimize a sum of squared differences between the theoretical X-ray attenuation values and the actual X-ray attenuation values corresponding to different angles at each of the channels, and use the obtained value as the equivalent filtration thicknesses corresponding to each of the channels.

In another example, the device may further include a center point determining module and a length calculating module.

The center point determining module is used to determine an intersection point of two channels respectively corresponding to maximum actual X-ray attenuation values at two angles as a center point of the universal phantom.

The length calculating module is used to determine the lengths of the universal phantom passed by X-ray beams corresponding to different angles and each of the channels according to the center point of the universal phantom, a rotation center and a position of the bulb.

In an example, the data generating module 303 may generate hardening effect data corresponding to two or more materials based on the following equation:

$$P_k(L_1, \ldots, L_M) = \ln\left(\sum_{i=1}^{N} I_0(i) * \exp(-\mu_{filter}(i) * L_{filter,k} - \mu_{filter}(i) * (D - L_{filter,k}))\right) -$$

$$\ln\left(\sum_{i=1}^{N} I_0(i) * \exp\right.$$

$$\left.(-\mu_{filter}(i) * L_{filter,k} - \mu_{air}(i) * L_{air} - \mu_1(i) * L_1 \ldots - \mu_M(i) * L_M).$$

Herein $P_k(L_1, \ldots, L_M)$ represents the hardening effect data corresponding to M materials at the $k^{th}$ channel, k represents a channel index, M represents a number of species of materials, and M is an integer greater than 1;

$I_0(i)$ represents the $i^{th}$ spectral intensity value of X-ray beam emitted by the bulb, i=1~N, and N represents an aliquot number of X photons with various energy levels contained in the X-ray beam;

$\mu_{filter}(i)$ represents an attenuation coefficient of the $i^{th}$ spectrum corresponding to a filter;

$L_{filter,k}$ represents the equivalent filtration thickness corresponding to the $k^{th}$ channel;

$\mu_{air}(i)$ represents an attenuation coefficient of the $i^{th}$ spectrum corresponding to air;

$\mu_1(i)$ represents an attenuation coefficient of the $i^{th}$ spectrum corresponding to the first material;

$\mu_M(i)$ represents an attenuation coefficient of the $i^{th}$ spectrum corresponding to the $M^{th}$ material;

$L_1$ represents a predetermined length of the first material, and $L_M$ represents a predetermined length of the $M^{th}$ material;

$L_{air}$ represents a predetermined length of air; and

D represents a distance between the bulb and a detector.

In another example, the data generating module 303 may generate hardening effect data corresponding to a material based on the following equation:

$$P_k(L_1) = \ln\left(\sum_{i=1}^{N} I_0(i) * \exp(-\mu_{filter}(i) * L_{filter,k} - \mu_{filter}(i) * (D - L_{filter,k}))\right) -$$

$$\ln\left(\sum_{i=1}^{N} I_0(i) * \exp(-\mu_{filter}(i) * L_{filter,k} - \mu_{air}(i) * L_{air} - \mu_1(i) * L_1)\right).$$

Herein $P_k(L_1)$ represents the hardening effect data corresponding to the material at the $k^{th}$ channel, and k represents a channel index;

$I_0(i)$ represents the $i^{th}$ spectral intensity value of X-ray beam emitted by the bulb, i=1~N, and N represents an aliquot number of X photons with various energy levels contained in the X-ray beam;

$\mu_{filter}(i)$ represents an attenuation coefficient of the $i^{th}$ spectrum corresponding to a filter;

$L_{filter,k}$ represents the equivalent filtration thickness corresponding to the $k^{th}$ channel;

$\mu_{air}(i)$ represents an attenuation coefficient of the $i^{th}$ spectrum corresponding to air;

$\mu_1(i)$ represents an attenuation coefficient of the $i^{th}$ spectrum corresponding to the material;

$L_1$ represents a predetermined length of the material;

$L_{air}$ represents a predetermined length of air; and

D represents a distance between the bulb and a detector.

Figure 7:
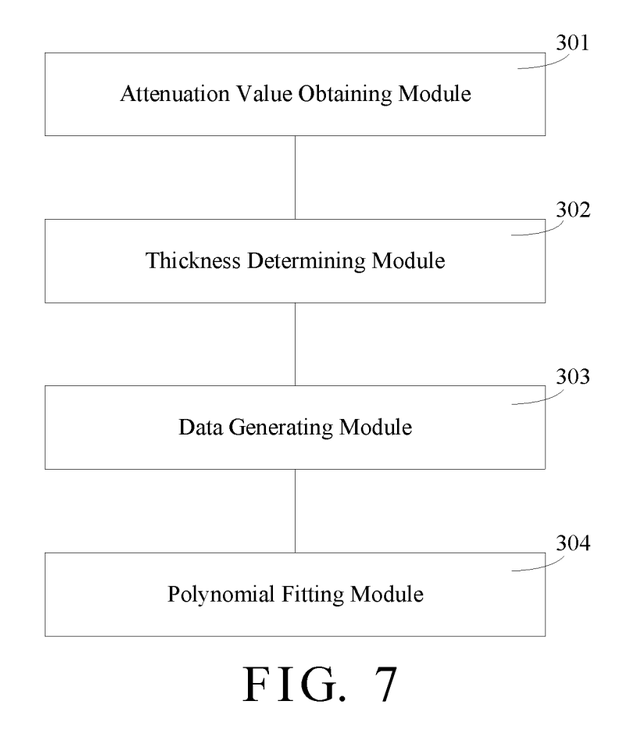
FIG. 7 is a block diagram of the control logic for generating material hardening effect data according to another example of the present disclosure.

FIG. 7 is a block diagram of the control logic for generating material hardening effect data according to another example of the present disclosure. Be compared with FIG. 6, the control logic 30 may further include a polynomial fitting module 304.

The polynomial fitting module 304 is used to, according to the hardening effect data corresponding to the material, fit a mathematical relationship between a material path length and a hardening effect attenuation value by using a polynomial fitting algorithm.

The example below is implemented with software, which describes how the device for generating material hardening effect data runs the control logic 30. In this example, the control logic 30 of the present disclosure should be understood as machine readable instructions stored in the machine readable storage medium 52. When the processor 51 of the device executes the control logic 30, the processor 51 may execute machine readable instructions of the control logic 30 stored in the machine readable storage medium 52 to:

obtain actual X-ray attenuation values of a universal phantom corresponding to different angles at each of channels;

determine equivalent filtration thicknesses corresponding to each of the channels according to theoretical X-ray attenuation values and the actual X-ray attenuation values corresponding to different angles at each of the channels; and generate hardening effect data corresponding to a material according to a predetermined length of the material, a number of sampling points and the equivalent filtration thicknesses corresponding to each of the channels.

Furthermore, said machine readable instructions of the control logic 30 may further cause the processor 51 to:

according to the hardening effect data corresponding to the material, fit a mathematical relationship between a material path length and a hardening effect attenuation value by using a polynomial fitting algorithm.

According to an example, said machine readable instructions of the control logic 30 may further cause the processor 51 to:

determine the equivalent filtration thicknesses corresponding to each of the channels in such a way that may minimize errors between the theoretical X-ray attenuation values and the actual X-ray attenuation values corresponding to different angles at each of the channels.

According to another example, said machine readable instructions of the control logic 30 may further cause the processor 51 to:

establish a mathematical relationship of the theoretical X-ray attenuation values corresponding to different angles at each of the channels according to a spectral curve generated by a bulb under a scanning voltage, lengths of X-ray beams corresponding to different angles and each of the channels, a material spectral attenuation curve of the universal phantom, and the equivalent filtration thicknesses corresponding to each of the channels;

based on the mathematical relationship, obtain a value that may minimize a sum of squared differences between the theoretical X-ray attenuation values and the actual X-ray attenuation values corresponding to different angles at each of the channels, and use the obtained value as the equivalent filtration thicknesses corresponding to each of the channels.

According to another example, said machine readable instructions of the control logic 30 may further cause the processor 51 to:

according to two channels respectively corresponding to maximum actual X-ray attenuation values at two angles, determine an intersection point of the two channels as a center point of the universal phantom; and determine the lengths of the universal phantom passed by X-ray beams corresponding to different angles and each of the channels according to the center of the universal phantom, a rotation center and a position of the bulb.

According to an example, said machine readable instructions of the control logic 30 may further cause the processor 51 to:

generate hardening effect data corresponding to two or more materials based on the following equation:

$$P_k(L_1, \ldots, L_M) =$$

$$\ln\left(\sum_{i=1}^{N} I_0(i) * \exp(-\mu_{filter}(i) * L_{filter,k} - \mu_{filter}(i) * (D - L_{filter,k}))\right) -$$

$$\ln\left(\sum_{i=1}^{N} I_0(i) * \exp\right.$$

$$\left.(-\mu_{filter}(i) * L_{filter,k} - \mu_{air}(i) * L_{air} - \mu_1(i) * L_1 \ldots - \mu_M(i) * L_M)\right).$$

Herein $P_k(L_1, \ldots, L_M)$ represents the hardening effect data corresponding to M materials at the $k^{th}$ channel, k represents a channel index, M represents a number of species of materials, and M is an integer greater than 1;

$I_0(i)$ represents the $i^{th}$ spectral intensity value of X-ray beam emitted by the bulb, i=1~N, and N represents an aliquot number of X photons with various energy levels contained in the X-ray beam;

$\mu_{filter}(i)$ represents an attenuation coefficient of the $i^{th}$ spectrum corresponding to a filter;

$L_{filter,k}$ represents the equivalent filtration thickness corresponding to the $k^{th}$ channel;

$\mu_{air}(i)$ represents an attenuation coefficient of the $i^{th}$ spectrum corresponding to air;

$\mu_1(i)$ represents an attenuation coefficient of the $i^{th}$ spectrum corresponding to the first material;

$\mu_M(i)$ represents an attenuation coefficient of the $i^{th}$ spectrum corresponding to the $M^{th}$ material;

$L_1$ represents a predetermined length of the first material, and $L_M$ represents a predetermined length of the $M^{th}$ material;

$L_{air}$ represents a predetermined length of air; and

D represents a distance between the bulb and a detector.

According to another example, said machine readable instructions of the control logic 30 further causes the processor 51 to:

generate hardening effect data corresponding to a material based on the following equation:

$$P_k(L_1) = \ln\left(\sum_{i=1}^{N} I_0(i) * \exp(-\mu_{filter}(i) * L_{filter,k} - \mu_{filter}(i) * (D - L_{filter,k}))\right) - \ln\left(\sum_{i=1}^{N} I_0(i) * \exp(-\mu_{filter}(i) * L_{filter,k} - \mu_{air}(i) * L_{air} - \mu_1(i) * L_1)\right).$$

Herein $P_k(L_1)$ represents the hardening effect data corresponding to the material at the $k^{th}$ channel, and k represents a channel index;

$I_0(i)$ represents the $i^{th}$ spectral intensity value of X-ray beam emitted by the bulb, i=1~N, and N represents an aliquot number of X photons with various energy levels contained in the X-ray beam;

$\mu_{filter}(i)$ represents an attenuation coefficient of the $i^{th}$ spectrum corresponding to a filter;

$L_{filter,k}$ represents the equivalent filtration thickness corresponding to the $k^{th}$ channel;

$\mu_{air}(i)$ represents an attenuation coefficient of the $i^{th}$ spectrum corresponding to air;

$\mu_1(i)$ represents an attenuation coefficient of the $i^{th}$ spectrum corresponding to the material;

$L_1$ represents a predetermined length of the material;

$L_{air}$ represents a predetermined length of air; and

D represents a distance between the bulb and a detector.

The above are only preferred examples of the present disclosure is not intended to limit the disclosure within the spirit and principles of the present disclosure, any changes made, equivalent replacement, or improvement in the protection of the present disclosure should contain within the range.

The methods, processes and units described herein may be implemented by hardware (including hardware logic circuitry), software or firmware or a combination thereof. The term 'processor' is to be interpreted broadly to include a processing unit, ASIC, logic unit, or programmable gate array etc. The processes, methods and functional units may all be performed by the one or more processors; reference in this disclosure or the claims to a 'processor' should thus be interpreted to mean 'one or more processors'.

Further, the processes, methods and functional units described in this disclosure may be implemented in the form of a computer software product. The computer software product is stored in a storage medium and comprises a plurality of instructions for making a processor to implement the methods recited in the examples of the present disclosure.

The figures are only illustrations of an example, wherein the units or procedure shown in the figures are not necessarily essential for implementing the present disclosure. Those skilled in the art will understand that the units in the device in the example can be arranged in the device in the examples as described, or can be alternatively located in one or more devices different from that in the examples. The units in the examples described can be combined into one module or further divided into a plurality of sub-units.

Although the flowcharts described show a specific order of execution, the order of execution may differ from that which is depicted. For example, the order of execution of two or more blocks may be changed relative to the order shown. Also, two or more blocks shown in succession may be executed concurrently or with partial concurrence. All such variations are within the scope of the present disclosure.

Throughout the present disclosure, the word "comprise", or variations such as "comprises" or "comprising", will be understood to imply the inclusion of a stated element, integer or step, or group of elements, integers or steps, but not the exclusion of any other element, integer or step, or group of elements, integers or steps.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. A method for generating material hardening effect data, comprises:

obtaining actual X-ray attenuation values of a universal phantom corresponding to different angles at each of channels;

according to theoretical X-ray attenuation values and the actual X-ray attenuation values corresponding to different angles at each of the channels, determining equivalent filtration thicknesses corresponding to each of the channels in such a way that minimizes errors between the theoretical X-ray attenuation values and the actual X-ray attenuation values corresponding to different angles at each of the channels; and according to a predetermined length of a material, a number of sampling points and the equivalent filtration thicknesses corresponding to each of the channels, generating hardening effect data corresponding to the material.

2. The method of claim 1 wherein determining the equivalent filtration thicknesses corresponding to each of the channels in the way that minimizes errors between the theoretical X-ray attenuation values and the actual X-ray attenuation values corresponding to different angles at each of the channels comprises:

according to a spectral curve generated by a bulb under a scanning voltage, lengths of the universal phantom passed by X-ray beams corresponding to different angles and each of the channels, a material spectral attenuation curve of the universal phantom, and the equivalent filtration thicknesses corresponding to each of the channels, establishing a mathematical relationship of the theoretical X-ray attenuation values corresponding to different angles at each of the channels;

based on the mathematical relationship, obtaining a value that minimizes a sum of squared differences between the theoretical X-ray attenuation values and the actual X-ray attenuation values corresponding to different angles at each of the channels, and using the value as the equivalent filtration thicknesses corresponding to each of the channels.

3. The method of claim 2, wherein the lengths of the universal phantom passed by X-ray beams corresponding to different angles and each of the channels are determined by:

according to two channels respectively corresponding to maximum actual X-ray attenuation values at two angles, determining an intersection point of the two channels as a center point of the universal phantom; and according to the center point of the universal phantom, a rotation center and a position of the bulb, determining the lengths of the universal phantom passed by X-ray beams corresponding to different angles and each of the channels.

4. The method of claim 1, wherein generating the hardening effect data comprises:

generating hardening effect data corresponding to two or more materials based on following equation:

$$P_k(L_1, \ldots, L_M) = \ln\left(\sum_{i=1}^{N} I_0(i) * \exp(-\mu_{filter}(i) * L_{filter,k} - \mu_{filter}(i) * (D - L_{filter,k}))\right) - \ln\left(\sum_{i=1}^{N} I_0(i) * \exp\right.$$

$$\left.(-\mu_{filter}(i) * L_{filter,k} - \mu_{air}(i) * L_{air} - \mu_1(i) * L_1 \wedge \ldots - \mu_M(i) * L_M);\right.$$

wherein $P_k(L_1, \ldots, L_M)$ represents the hardening effect data corresponding to M materials at the $k^{th}$ channel, k represents a channel index, M represents a number of species of materials, and M is an integer greater than 1;

$I_0(i)$ represents the $i^{th}$ spectral intensity value of X-ray beam emitted by the bulb, i=1~N, and N represents an aliquot number of X photons with various energy levels contained in the X-ray beam;

$\mu_{filter}(i)$ represents an attenuation coefficient of the $i^{th}$ spectrum corresponding to a filter;

$L_{filter,k}$ represents the equivalent filtration thickness corresponding to the $k^{th}$ channel;

$\mu_{air}(i)$ represents an attenuation coefficient of the $i^{th}$ spectrum corresponding to air;

$\mu_1(i)$ represents an attenuation coefficient of the $i^{th}$ spectrum corresponding to the first material;

$\mu_M(i)$ represents an attenuation coefficient of the $i^{th}$ spectrum corresponding to the $M^{th}$ material;

$L_1$ represents a predetermined length of the first material, and $L_M$ represents a predetermined length of the $M^{th}$ material;

$L_{air}$ represents a predetermined length of air; and

D represents a distance between the bulb and a detector.

5. The method of claim 1, wherein generating the hardening effect data comprises:

generating hardening effect data corresponding to a material based on following equation:

$$P_k(L_1) = \ln\left(\sum_{i=1}^{N} I_0(i) * \exp(-\mu_{filter}(i) * L_{filter,k} - \mu_{filter}(i) * (D - L_{filter,k}))\right) -$$

$$\ln\left(\sum_{i=1}^{N} I_0(i) * \exp(-\mu_{filter}(i) * L_{filter,k} - \mu_{air}(i) * L_{air} - \mu_1(i) * L_1);\right.$$

wherein $P_k(L_1)$ represents the hardening effect data corresponding to the material at the $k^{th}$ channel, and k represents a channel index;

$I_0(i)$ represents the $i^{th}$ spectral intensity value of X-ray beam emitted by the bulb, i=1~N, and N represents an aliquot number of X photons with various energy levels contained in the X-ray beam;

$\mu_{filter}(i)$ represents an attenuation coefficient of the $i^{th}$ spectrum corresponding to a filter;

$L_{filter,k}$ represents the equivalent filtration thickness corresponding to the $k^{th}$ channel;

$\mu_{air}(i)$ represents an attenuation coefficient of the $i^{th}$ spectrum corresponding to air;

$\mu_1(i)$ represents an attenuation coefficient of the $i^{th}$ spectrum corresponding to the material;

$L_1$ represents a predetermined length of the material;

$L_{air}$ represents a predetermined length of air; and

D represents a distance between the bulb and a detector.

6. The method of claim 1, further comprises:

according to the hardening effect data corresponding to the material, fitting a mathematical relationship between a material path length and a hardening effect attenuation value by using a polynomial fitting algorithm.

7. A device for generating material hardening effect data, comprises:

a processor which invokes machine readable instructions corresponding to a control logic for generating material hardening effect data stored on a non-transitory storage medium and executes the machine readable instructions to:

obtain actual X-ray attenuation values of a universal phantom corresponding to different angles at each of channels;

according to theoretical X-ray attenuation values and the actual X-ray attenuation values corresponding to different angles at each of the channels, determine equivalent filtration thicknesses corresponding to each of the channels in such a way that minimizes errors between the theoretical X-ray attenuation values and the actual X-ray attenuation values corresponding to different angles at each of the channels; and according to a predetermined length of a material, a number of sampling points and the equivalent filtration thicknesses corresponding to each of the channels, generate hardening effect data corresponding to the material.

8. The device of claim 7, wherein said machine readable instructions further cause the processor to:

according to a spectral curve generated by a bulb under a scanning voltage, lengths of the universal phantom passed by X-ray beams corresponding to different angles and each of the channels, a material spectral attenuation curve of the universal phantom, and the equivalent filtration thicknesses corresponding to each of the channels, establish a mathematical relationship of the theoretical X-ray attenuation values corresponding to different angles at each of the channels;

based on the mathematical relationship, obtain a value that minimizes a sum of squared differences between the theoretical X-ray attenuation values and the actual X-ray attenuation values corresponding to different angles at each of the channels, and use the obtained value as the equivalent filtration thicknesses corresponding to each of the channels.

9. The device of claim 8, wherein said machine readable instructions further cause the processor to:

according to two channels respectively corresponding to maximum actual X-ray attenuation values at two angles, determine an intersection point of the two channels as a center point of the universal phantom; and according to the center point of the universal phantom, a rotation center and a position of the bulb, determine the lengths of the universal phantom passed by X-ray beams corresponding to different angles and each of the channels.

10. The device of claim 7, wherein said machine readable instructions further cause the processor to:

generate hardening effect data corresponding to two or more materials based on following equation:

$$P_k(L_1, \ldots, L_M) = \ln\left(\sum_{i=1}^{N} I_0(i) * \exp(-\mu_{filter}(i) * L_{filter,k} - \mu_{filter}(i) * (D - L_{filter,k}))\right) - \ln\left(\sum_{i=1}^{N} I_0(i) * \exp(-\mu_{filter}(i) * L_{filter,k} - \mu_{air}(i) * L_{air} - \mu_1(i) * L_1 \wedge \ldots - \mu_M(i) * L_M)\right);$$

wherein $P_k(L_1, \ldots, L_M)$ represents the hardening effect data corresponding to M materials at the $k^{th}$ channel, k represents a channel index, M represents a number of species of materials, and M is an integer greater than 1;

$I_0(i)$ represents the $i^{th}$ spectral intensity value of X-ray beam emitted by the bulb, $i=1{\sim}N$, and N represents an aliquot number of X photons with various energy levels contained in the X-ray beam;

$\mu_{filter}(i)$ represents an attenuation coefficient of the $i^{th}$ spectrum corresponding to a filter;

$L_{filter,k}$ represents the equivalent filtration thickness corresponding to the $k^{th}$ channel;

$\mu_{air}(i)$ represents an attenuation coefficient of the $i^{th}$ spectrum corresponding to air;

$\mu_1(i)$ represents an attenuation coefficient of the $i^{th}$ spectrum corresponding to the first material;

$\mu_M(i)$ represents an attenuation coefficient of the $i^{th}$ spectrum corresponding to the $M^{th}$ material;

$L_1$ represents a predetermined length of the first material, and $L_M$ represents a predetermined length of the $M^{th}$ material;

$L_{air}$ represents a predetermined length of air; and

D represents a distance between the bulb and a detector.

11. The device of claim 7, wherein said machine readable instructions further cause the processor to:

generate hardening effect data corresponding to a material based on following equation:

$$P_k(L_1) = \ln\left(\sum_{i=1}^{N} I_0(i) * \exp(-\mu_{filter}(i) * L_{filter,k} - \mu_{filter}(i) * (D - L_{filter,k}))\right) - \ln\left(\sum_{i=1}^{N} I_0(i) * \exp(-\mu_{filter}(i) * L_{filter,k} - \mu_{air}(i) * L_{air} - \mu_1(i) * L_1\right);$$

wherein $P_k(L_1)$ represents the hardening effect data corresponding to the material at the $k^{th}$ channel, and k represents a channel index;

$I_0(i)$ represents the $i^{th}$ spectral intensity value of X-ray beam emitted by the bulb, $i=1{\sim}N$, and N represents an aliquot number of X photons with various energy levels contained in the X-ray beam;

$\mu_{filter}(i)$ represents an attenuation coefficient of the $i^{th}$ spectrum corresponding to a filter;

$L_{filter,k}$ represents the equivalent filtration thickness corresponding to the $k^{th}$ channel;

$\mu_{air}(i)$ represents an attenuation coefficient of the $i^{th}$ spectrum corresponding to air;

$\mu_1(i)$ represents an attenuation coefficient of the $i^{th}$ spectrum corresponding to the material;

$L_1$ represents a predetermined length of the material;

$L_{air}$ represents a predetermined length of air; and

D represents a distance between the bulb and a detector.

12. The device of claim 7, wherein said machine readable instructions further cause the processor to:

according to the hardening effect data corresponding to the material, fit a mathematical relationship between a material path length and a hardening effect attenuation value by using a polynomial fitting algorithm.

* * * * *